(12) United States Patent
Toler

(10) Patent No.: US 10,952,755 B2
(45) Date of Patent: *Mar. 23, 2021

(54) GAP REFERENCING FEMORAL SIZER

(71) Applicant: Zimmer, Inc., Warsaw, IN (US)

(72) Inventor: Jason S. Toler, Pierceton, IN (US)

(73) Assignee: Zimmer, Inc., Warsaw, IN (US)

( * ) Notice: Subject to any disclaimer, the term of this patent is extended or adjusted under 35 U.S.C. 154(b) by 300 days.

This patent is subject to a terminal disclaimer.

(21) Appl. No.: 16/108,861

(22) Filed: Aug. 22, 2018

(65) Prior Publication Data

US 2018/0360478 A1 Dec. 20, 2018

Related U.S. Application Data

(63) Continuation of application No. 14/880,522, filed on Oct. 12, 2015, now Pat. No. 10,076,344.

(Continued)

(51) Int. Cl.
*A61B 17/17* (2006.01)
*A61B 17/88* (2006.01)
(Continued)

(52) U.S. Cl.
CPC ........ *A61B 17/1764* (2013.01); *A61B 17/025* (2013.01); *A61B 17/155* (2013.01);
(Continued)

(58) Field of Classification Search
CPC ................ A61B 17/1764; A61B 17/88; A61F 2/4657–2002/4668
See application file for complete search history.

(56) References Cited

U.S. PATENT DOCUMENTS 5,860,980 A 1/1999 Axelson, Jr. et al.
5,911,723 A 6/1999 Ashby et al.
(Continued)

FOREIGN PATENT DOCUMENTS

CN 107106189 A 8/2017
FR 2949315 A1 4/2011
(Continued)

OTHER PUBLICATIONS

"Chinese Application Serial No. 201580071677.7, Response filed Jun. 25, 2019 to Office Action dated Feb. 28, 2019", with English claims, 11 pages.

(Continued)

*Primary Examiner* — Zade Coley
(74) *Attorney, Agent, or Firm* — Schwegman Lundberg & Woessner, P.A.

(57) ABSTRACT

A knee arthroplasty assembly for use in a patient's knee joint including a tibia and a femur is disclosed. The assembly can include a tool, a first accessory, and a second accessory. The tool can include a tibial component configured for placement against the tibia and a femoral component configured for placement against the femur. The femoral component can be moveably coupled to the tibial component to place the patient's knee joint in tension by separating the tibia and the femur. The first accessory can be removeably coupled to the tibial component of the tool. The second accessory can be referenced to the first accessory and can have a reference indicator that references the femur for determining a size of the femur.

16 Claims, 10 Drawing Sheets

Related U.S. Application Data

(60) Provisional application No. 62/081,793, filed on Nov. 19, 2014.

(51) Int. Cl.
    *A61F 2/46*           (2006.01)
    *A61B 17/02*         (2006.01)
    *A61B 17/15*         (2006.01)
    *A61B 90/00*         (2016.01)
    *A61B 17/90*         (2006.01)

(52) U.S. Cl.
    CPC .............. *A61B 17/88* (2013.01); *A61B 90/06* (2016.02); *A61F 2/4657* (2013.01); *A61B 2017/0268* (2013.01); *A61B 2017/90* (2013.01); *A61B 2090/061* (2016.02); *A61B 2090/067* (2016.02); *A61F 2002/4658* (2013.01)

(56) References Cited

U.S. PATENT DOCUMENTS

| | | | |
|---|---|---|---|
| 6,056,756 A * | 5/2000 | Eng ...................... | A61B 17/155 606/87 |
| 7,156,853 B2 * | 1/2007 | Muratsu ............. | A61B 17/0206 606/102 |
| 9,050,197 B2 * | 6/2015 | Lorio .................... | A61F 2/4657 |
| 10,076,344 B2 | 9/2018 | Toler | |
| 10,166,034 B2 | 1/2019 | Claypool et al. | |
| 2004/0122441 A1 | 6/2004 | Muratsu | |
| 2005/0256527 A1 | 11/2005 | Delfosse et al. | |
| 2007/0173851 A1 * | 7/2007 | McMillen ............. | A61F 2/4657 606/87 |
| 2007/0293868 A1 | 12/2007 | Delfosse et al. | |
| 2009/0138021 A1 | 5/2009 | Colquhoun et al. | |
| 2011/0046685 A1 * | 2/2011 | Faure .................... | A61F 2/4657 606/86 R |
| 2013/0144302 A1 * | 6/2013 | Reeve ................... | A61B 17/15 606/102 |
| 2014/0025081 A1 * | 1/2014 | Lorio ........................ | A61F 2/38 606/102 |
| 2014/0228853 A1 | 8/2014 | Rock | |
| 2014/0288563 A1 | 9/2014 | Claypool et al. | |
| 2016/0135825 A1 | 5/2016 | Toler | |

FOREIGN PATENT DOCUMENTS

| | | | | |
|---|---|---|---|---|
| JP | 8229058 | A | 9/1996 | |
| JP | 11113940 | A | 4/1999 | |
| JP | 2001517135 | A | 10/2001 | |
| JP | 2004237064 | A | 8/2004 | |
| JP | 2014524815 | A | 9/2014 | |
| JP | 6055825 | B2 | 12/2016 | |
| WO | WO-0185038 | A1 | 11/2001 | |
| WO | WO-2007036694 | A1 | 4/2007 | |
| WO | WO 2013013094 | | * 1/2013 | ......... A61B 17/1764 |
| WO | WO-2013013094 | A1 | 1/2013 | |
| WO | WO-2014006360 | A1 | 1/2014 | |
| WO | WO-2016081094 | A1 | 5/2016 | |

OTHER PUBLICATIONS

"European Application Serial No. 17159428.6, Response filed Dec. 29, 2018 to Extended European Search Report dated May 2, 2018", 24 pgs.
"Chinese Application Serial No. 201580071677.7, Office Action dated Feb. 28, 2019", w English translation, 10 pgs.
"European Application Serial No. 15790721.3, Response Filed Jan. 14, 2019 to Communication Pursuant to Article 94(3) EPC dated Sep. 5, 2018", 5 pgs.
"U.S. Appl. No. 14/233,227, Notice of Allowance dated Aug. 15, 2018", 7 pgs.
"European Application Serial No. 15790721.3, Communication Pursuant to Article 94(3) EPC dated Sep. 5, 2018", 5 pgs.
"U.S. Appl. No. 14/233,227, Final Office Action dated May 25, 2018", 12 pgs.
"U.S. Appl. No. 14/233,227, Non Final Office Action dated Jan. 24, 2018", 12 pgs.
"U.S. Appl. No. 14/233,227, Preliminary Amendment dated Jan. 16, 2014", 9 pgs.
"U.S. Appl. No. 14/233,227, Response Filed Apr. 23, 2018 to Non-Final Office Action dated Jan. 24, 2018", 14 pgs.
"U.S. Appl. No. 14/233,227, Response Filed Jul. 25, 2018 to Final Office Action dated May 25, 2018", 10 pgs.
"U.S. Appl. No. 14/233,227, Response filed Oct. 19, 2017 to Restriction Requirement dated Aug. 24, 2017", 9 pgs.
"U.S. Appl. No. 14/233,227, Restriction Requirement dated Aug. 24, 2017", 9 pgs.
"U.S. Appl. No. 14/880,522, Non Final Office Action dated Jan. 16, 2018", 11 pgs.
"U.S. Appl. No. 14/880,522, Notice of Allowability dated Jun. 15, 2018", 2 pgs.
"U.S. Appl. No. 14/880,522, Notice of Allowance dated May 23, 2018", 7 pgs.
"U.S. Appl. No. 14/880,522, Response filed Mar. 30, 2018 to Non Final Office Action dated Jan. 16, 2018", 11 pgs.
"U.S. Appl. No. 14/880,522, Response filed Dec. 19, 2017 to Restriction Requirement dated Oct. 20, 2017", 8 pgs.
"U.S. Appl. No. 14/880,522, Restriction Requirement dated Oct. 20, 2017", 6 pgs.
"Attune Surgical Technique", DePuy Orthopaedics Inc., (2012), 31 pgs.
"European Application Serial No. 12741216.1, Communication Pursuant to Article 94(3) EPC dated Jan. 8, 2016", 6 pgs.
"European Application Serial No. 12741216.1, Response filed Jul. 18, 2016 to Communication Pursuant to Article 94(3) EPC dated Jan. 8, 2016", 15 pgs.
"European Application Serial No. 12741216.1, Response filed Sep. 29, 2014 to Communication pursuant to Rules 161(1) and 162 EPC dated Mar. 19, 2014", 14 pgs.
"European Application Serial No. 15790721.3, Response filed Feb. 12, 2018 to Action dated Aug. 1, 2017", 13 pgs.
"European Application Serial No. 17159428.6, Extended European Search Report dated May 2, 2018", 11 pgs.
"Flexion/Extension Gap Balancing Surgical Technique Addendum", Smith & Nephew Journey BCS Bi-Cruciate Stabilized Knee System, (Jan. 2008), 4 pgs.
"International Application Serial No. PCT/US2012/047479, International Preliminary Report on Patentability dated Jan. 30, 2014", 9 pgs.
"International Application Serial No. PCT/US2012/047479, Search Report dated Sep. 10, 2012", 10 pgs.
"International Application Serial No. PCT/US2012/047479, Written Opinion dated Sep. 10, 2012", 7 pgs.
"International Application Serial No. PCT/US2015/055087, International Preliminary Report on Patentability dated Jun. 1, 2017", 9 pgs.
"International Application Serial No. PCT/US2015/055087, International Search Report dated Jan. 21, 2016", 7 pgs.
"International Application Serial No. PCT/US2015/055087, Written Opinion dated Jan. 21, 2016", 7 pgs.
"Japanese Application Serial No. 2014-521804, Amendment filed Jun. 23, 2015", (W/ English Translation), 7 pgs.
"Japanese Application Serial No. 2014-521804, Office Action dated Jul. 5, 2016", (W/ English Translation), 8 pgs.
"Japanese Application Serial No. 2014-521804, Response filed Sep. 13, 2016 to Office Action dated Jul. 5, 2016", (English Translation of Claims), 17 pgs.
"Triathlon Knee System Gap Balancing Technique Surgical Protocol Addendum", Stryker Orthopaedics, Literature No. LSPK55, (2010), 8 pgs.

* cited by examiner

GAP REFERENCING FEMORAL SIZER

CLAIM OF PRIORITY

This application is a continuation of U.S. patent application Ser. No. 14/880,522, filed on Oct. 12, 2015, which claims the benefit of U.S. Provisional Patent Application Ser. No. 62/081,793, filed on Nov. 19, 2014, the benefit of priority of each of which is claimed hereby, and which is incorporated by reference herein in its entirety.

TECHNICAL FIELD

The present disclosure relates to knee arthroplasty. More particularly, the present disclosure relates to an instrument for use during a knee arthroplasty procedure, and to systems and methods for using the same.

BACKGROUND

In a total knee arthroplasty (TKA) procedure, a patient's distal femur is resected and replaced with a prosthetic femoral implant, and the patient's proximal tibia is resected and replaced with a prosthetic tibial implant. The prosthetic femoral implant articulates with the prosthetic tibial implant to restore joint motion.

Many factors influence joint motion after the TKA procedure. The size and shape of each prosthetic implant will impact joint motion. Additionally, the location and orientation of each prosthetic implant, which is determined by the location and orientation of the corresponding bone resections, will impact joint motion. The tension or laxity of the surrounding soft tissue will also impact joint motion. For example, if the surrounding collateral ligaments are too tense, joint motion may be limited, but if the surrounding collateral ligaments are too lax, improper femoral rotation or femoral lift-off may occur. Also, the soft tissue balance around the joint will impact joint motion.

OVERVIEW

The present patent application provides an exemplary TKA instrument and procedure. The instrument can separate the patient's tibia and femur, in both extension and flexion, to place the knee joint in tension and to measure a gap and an angle therebetween. The instrument can include various modular accessory components. The components can provide flexibility of usage throughout the TKA procedure. For example, the instrument can be used before resecting or otherwise manipulating the patient's knee joint to evaluate the natural knee joint and plan the TKA procedure, as well as after resecting or otherwise manipulating the patient's knee joint to evaluate and/or further plan the TKA procedure.

In some TKA procedures, there is no uncomplicated way to size the femur if a gap balancing technique is utilized. This is because traditional femoral sizers measure the anterior to posterior distance referenced from the posterior condyles to the anterior cortex. However, if an amount (thickness) of a posterior resection of the posterior condyles is not the same as a thickness of a femoral implant, the anterior to posterior distance measured by the traditional gap sizer is no longer accurate. When gap balancing, the amount of posterior resection is varied in order to achieve a flexion gap that matches a previously resected extension gap. For example, if the extension gap is relatively large, more posterior bone can be resected to increase the flexion gap in order to match the extension gap, and thus, a smaller femoral component can be utilized. Similarly, if the extension gap is relatively small, less posterior bone can be resected to decrease the flexion gap, and thus, a larger femoral component can be utilized. Traditional gap sizers require the surgeon to recognize this matching issue including determinative sizing repercussions and adjust the size of a femoral implant accordingly. This adds complexity and time to the procedure.

The present inventor has recognized that the complexity of TKA procedures using the gap balancing technique can be reduced by providing a femoral sizer that can utilize the intended flexion gap height as the posterior reference point for femoral measurement rather than the posterior condyles. Thus, the sizer provides a method that can size the femur while accommodating a varying amount of posterior resection. In some examples, the femoral sizer can be one of the modular accessory components that attach to the TKA instrument to increase functionality and provide flexibility of usage throughout the TKA procedure. In particular, in some cases the femoral sizer can attach to one or more drill holes of a gap referencing drill guide. The drill guide itself can be one of the modular accessory components of the TKA instrument discussed previously. The femoral sizer can utilize the drill hole(s) in the drill guide (also referred to herein as a gap sizer) as a reference point when determining femoral size. This enables the femoral sizer to determine the size of the femur based on a desired flexion gap, independent of the posterior condyles, which no longer need to serve as the reference surfaces. Thus, the complexity of TKA procedures using the gap balancing technique can be reduced as the matching issues previously discussed are reduced or substantially eliminated.

According to an example of the present disclosure, a knee arthroplasty assembly for use in a patient's knee joint, the knee joint including a tibia and a femur, is disclosed. The assembly can include a tool, a first accessory, and a second accessory. The tool can include a tibial component configured for placement against the tibia and a femoral component configured for placement against the femur. The femoral component can be moveably coupled to the tibial component to place the patient's knee joint in tension by separating the tibia and the femur. The first accessory can be removeably coupled to the tibial component of the tool. The second accessory can be referenced to the first accessory component and can have a reference indicator that references the femur for determining a size of the femur.

According to another example of the present disclosure, a knee arthroplasty system for use in a patient's knee joint, the knee joint including a tibia and a femur, is disclosed. The system can include a tool, a first accessory, and a second accessory. The first accessory can be configured to be removeably coupled to the tibial component of the tool. The second accessory can be configured to reference the first accessory. A third accessory can be configured to be moveably coupled to the second accessory. The second accessory can have a first reference indicator and the third accessory can have a second reference indicator. Together, the first reference indicator and second reference indicator can reference the femur for determining a size of the femur.

According to yet another example of the present disclosure, a method of using a knee arthroplasty instrument on a knee joint is disclosed. The method can include inserting the instrument into a gap separating a tibia and a femur, including positioning a tibial component of the instrument adjacent the tibia and positioning a femoral component of the instrument adjacent the femur, adjusting the instrument to place the patient's knee joint in tension by separating the tibia and the femur, mounting a first sizer to the tibial component, the first sizer adapted for referencing the femur with respect to the tibial component, coupling a second sizer to the first sizer, and determining a size of the femur with a reference indicator of the second sizer, wherein the second sizer references the femur from the first sizer.

To further illustrate the knee arthroplasty assembly, system and method disclosed herein, a non-limiting list of examples is provided here:

In Example 1, a knee arthroplasty assembly for use in a patient's knee joint, the knee joint including a tibia and a femur, is disclosed. The assembly can include a tool, a first accessory, and a second accessory. The tool can include a tibial component configured for placement against the tibia and a femoral component configured for placement against the femur. The femoral component can be moveably coupled to the tibial component to place the patient's knee joint in tension by separating the tibia and the femur. The first accessory can be removeably coupled to the tibial component of the tool. The second accessory can be referenced to the first accessory component and can have a reference indicator that references the femur for determining a size of the femur.

In Example 2, the knee arthroplasty assembly of Example 1, wherein the second accessory can be configured to be coupled to the first accessory, and wherein determining the size of the femur may not include having to determine a size of a posterior condyle of the femur.

In Example 3, the knee arthroplasty assembly of any combination or any one of Examples 1-2, wherein the first accessory can comprise a drill guide.

In Example 4, the knee arthroplasty assembly of any combination or any one of Examples 1-3, wherein wherein the first accessory and second accessory can be at least one of rotatably and translationally fixed relative to the tibial component such that the femoral component can be capable of one or more of rotation and translation relative to the first accessory and the second accessory.

In Example 5, the knee arthroplasty assembly of any combination or any one of Examples 1-4, further comprising a third accessory that can be configured to be moveably coupled to the second accessory and can have a second reference indicator that corresponds with the reference indictor of the second accessory to size the femur.

In Example 6, the knee arthroplasty assembly of any combination or any one of Examples 1-5, wherein the third assembly can be rotatable and translatable relative to the second assembly.

In Example 7, the knee arthroplasty assembly of any combination or any one of Examples 1-6, wherein the third accessory can comprise a stylus, the stylus can comprise a first component having at least one post that can be configured to be received in a receptacle of the second accessory and can be moveable within the receptacle relative to the second accessory, and a second component that can be adapted for anterior referencing and that can be moveably coupled to the first component and can be configured to contact an anterior surface of the femur at or adjacent an anterior cortex of the femur.

In Example 8, the knee arthroplasty assembly of any combination or any one of Examples 1-7, wherein the second component can comprise a body having first and second tangs that define a guide track adapted to receive a portion of the first component and a knob configured to selectively exert force on the first and second tangs to force the first and second tangs against the first component.

In Example 9, the knee arthroplasty assembly of any combination or any one of Examples 1-8, wherein the second accessory can comprise a body having at least one receptacle adapted to receive a portion of a third accessory therein, and at least one pin extending from the body and adapted to be received in the first accessory, and wherein the reference indicator comprises a sizing scale disposed along a face of the second accessory.

In Example 10, the knee arthroplasty assembly of any combination or any one of Examples 1-9, wherein the second accessory can be configured to be coupled to the first accessory by a pin that is insertable within a hole that comprises a reference indicator of the first accessory.

In Example 11, a knee arthroplasty system for use in a patient's knee joint, the knee joint including a tibia and a femur, is disclosed. The system can include a tool, a first accessory, and a second accessory. The first accessory can be configured to be removeably coupled to the tibial component of the tool. The second accessory can be configured to reference the first accessory. A third accessory can be configured to be moveably coupled to the second accessory. The second accessory can have a first reference indicator and the third accessory can have a second reference indicator. Together, the first reference indicator and second reference indicator can reference the femur for determining a size of the femur.

In Example 12, the knee arthroplasty assembly of Example 11, wherein the third accessory can comprise a stylus comprising a first component having at least one post configured to be received in a receptacle of the second accessory and moveable within the receptacle relative to the second accessory, and a second component adapted for anterior referencing and being moveably coupled to the first component and configured to contact an anterior surface of the femur at or adjacent an anterior cortex of the femur.

In Example 13, the knee arthroplasty assembly of any combination or any one of Examples 11-12, wherein the second component can comprise a body having first and second tangs that define a guide track adapted to receive a portion of the first component, and a knob configured to selectively exert force on the first and second tangs to firmly abut the first and second tangs against the first component.

In Example 14, the knee arthroplasty assembly of any combination or any one of Examples 11-13, wherein the second accessory can comprise a body having at least one receptacle adapted to receive a portion of a third accessory therein, and at least one pin extending from the body and adapted to be received in the first accessory, and wherein the reference indicator comprises a sizing scale disposed along a face of the second accessory.

In Example 15, the knee arthroplasty assembly of any combination or any one of Examples 11-14, wherein the second accessory can be configured to be coupled to the first accessory by a pin that is insertable within a hole that comprises a reference indicator of the first accessory.

In Example 16, a method of using a knee arthroplasty instrument on a knee joint is disclosed. The method can include inserting the instrument into a gap separating a tibia and a femur, including positioning a tibial component of the instrument adjacent the tibia and positioning a femoral component of the instrument adjacent the femur, adjusting the instrument to place the patient's knee joint in tension by separating the tibia and the femur, mounting a first sizer to the tibial component, the first sizer adapted for referencing the femur with respect to the tibial component, coupling a second sizer to the first sizer, and determining a size of the femur with a reference indicator of the second sizer, wherein the second sizer references the femur from the first sizer.

In Example 17, the method of Example 16, wherein determining the size of the femur may not include determining a size of a posterior condyle of the femur.

In Example 18, the method of any combination or any one of Examples 16-17, wherein wherein coupling the second sizer to the first sizer can comprise inserting a portion of the second sizer in one or more holes of the first sizer, wherein the at least one of the one or more holes can be used as a drill locator.

In Example 19, the method of any combination or any one of Examples 16-18, can further comprise one or more of inserting a drill through at least one of the one or more holes, operating the drill to form one or more apertures in the femur, attaching a cut guide to the one or more apertures in the femur, and performing a posterior femoral resection of the femur utilizing the cut guide.

In Example 20, the method of any combination or any one of Examples 16-19, can further comprise attaching a moveable stylus assembly to the second sizer, the stylus assembly having a component adapted for anterior referencing including a guide track and a head adapted for contact with an anterior surface of the femur at or adjacent an anterior cortex of the femur.

In Example 21, the apparatus, system, or method of any one or any combination of Examples 1-20 can optionally be configured such that all elements or options recited are available to use or select from.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, like numerals can be used to describe similar elements throughout the several views. The drawings illustrate generally, by way of example, but not by way of limitation, various examples discussed in the present document.

DETAILED DESCRIPTION

Figure 1:
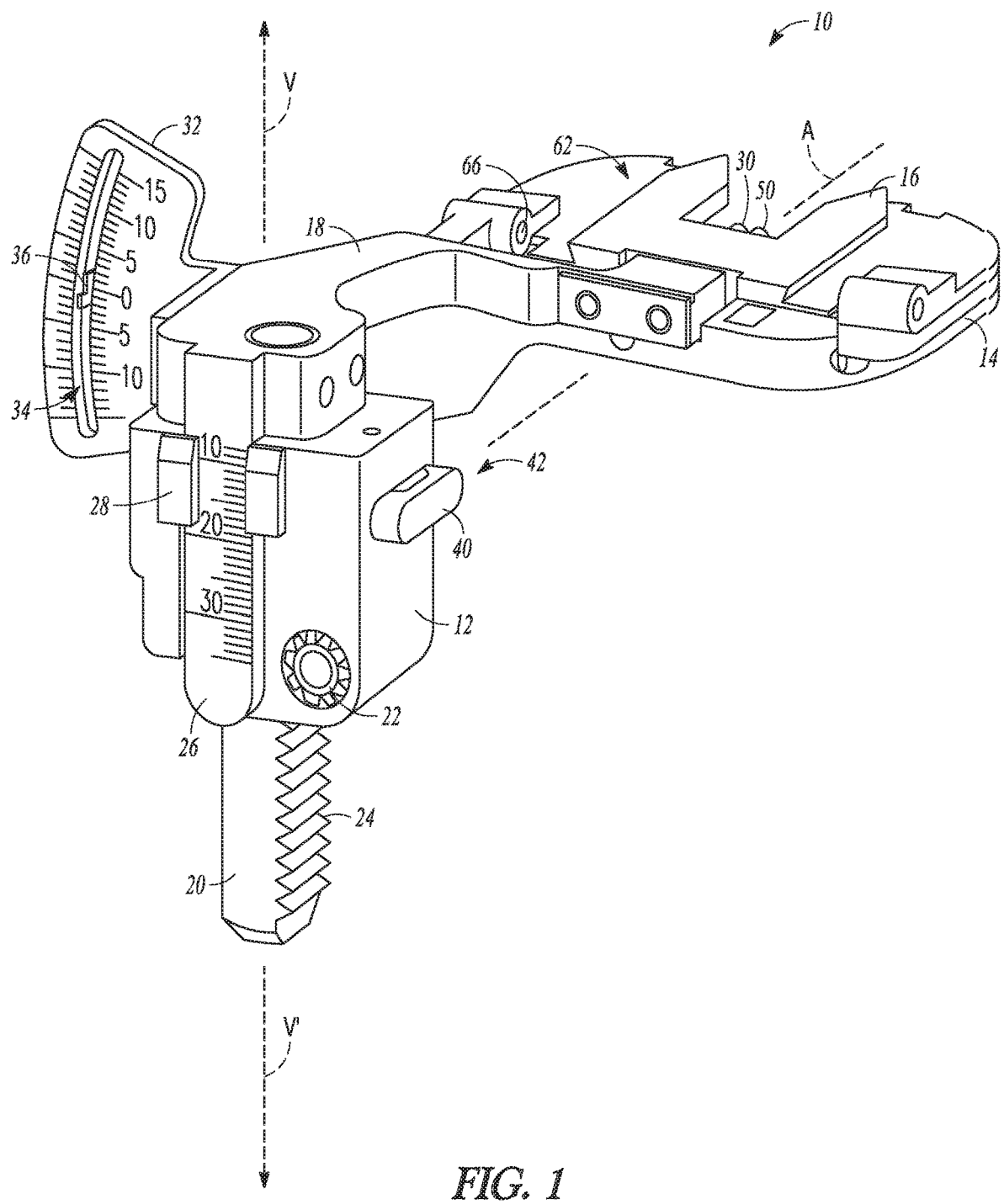
FIG. 1 is a perspective view of a knee arthroplasty instrument in accordance with an example of the present disclosure, the instrument including a base, a lower tibial component, an upper femoral component and an intermediate arm.
Figure 2:
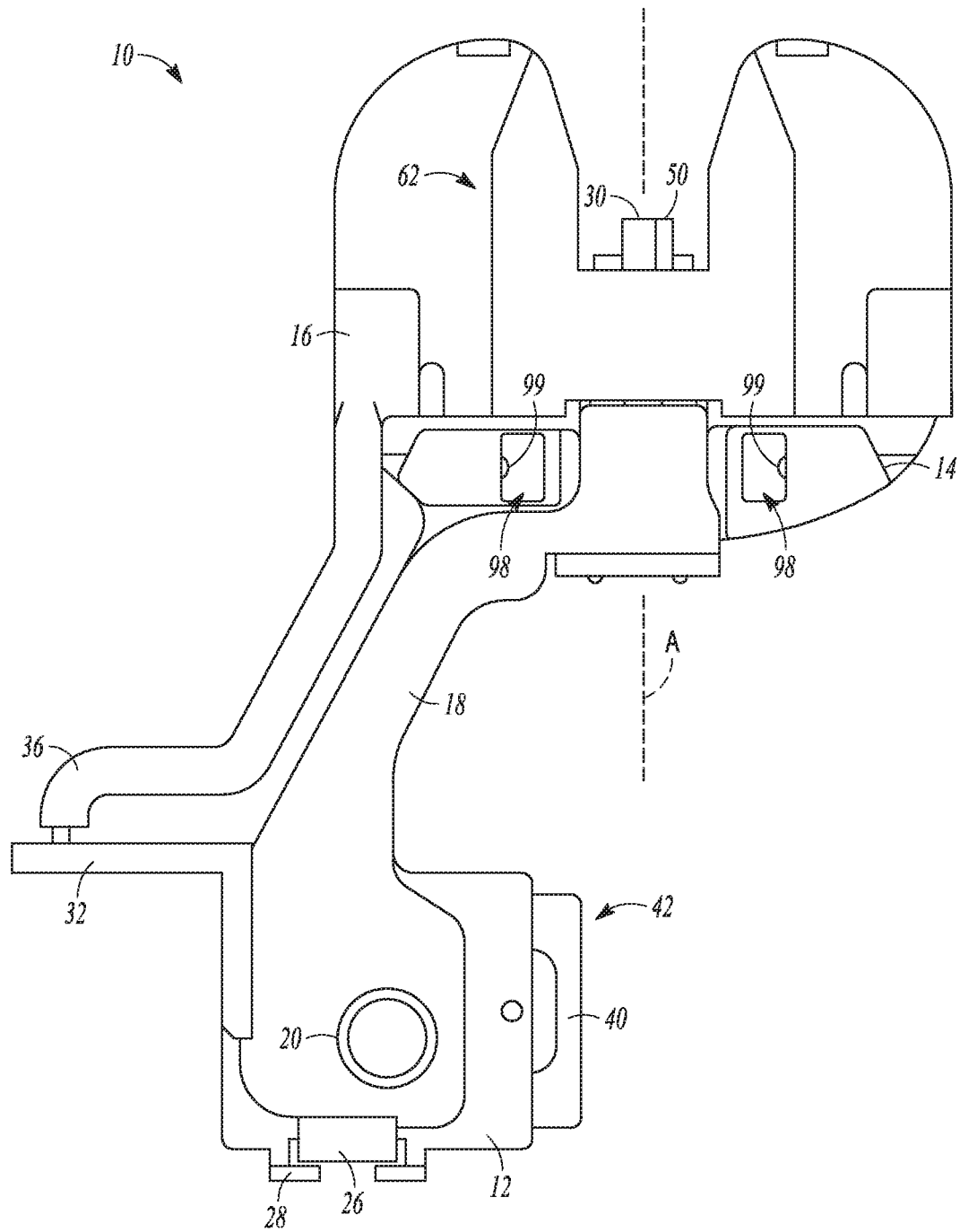
FIG. 2 is a top plan view of the instrument of FIG. 1, in accordance with an example of the present disclosure.

With reference to FIGS. 1 and 2, an instrument 10 can be provided for separating a patient's tibia and femur and measuring a joint gap and a joint angle therebetween. Instrument 10 can include a base portion 12, a lower tibial component 14, an upper femoral component 16, and an intermediate arm 18 configured to couple the tibial component 14 to the femoral component 16. Tibial component 14 and femoral component 16 are illustratively offset from base 12, as shown in FIG. 2, so they can accommodate the patient's patella. Additional information regarding a similar instrument may be found in U.S. Pat. No. 7,156,853 to Muratsu, the disclosure of which is incorporated herein by reference in its entirety.

Femoral component 16 can be configured to translate vertically along arrows V, V' relative to tibial component 14 via arm 18, as shown in FIG. 1. Instrument 10 can be opened by moving femoral component 16 apart from tibial component 14 along arrow V', and instrument 10 can be closed by moving femoral component 16 toward tibial component 14 along arrow V. As shown in FIGS. 1 and 2, arm 18 can include shaft 20 that translates vertically through base 12. Femoral component 16 can be coupled to arm 18 for movement therewith relative to base 12. Shaft 20 can be keyed to base 12 to permit vertical translation of shaft 20 through base 12 while preventing rotation of shaft 20 in base 12.

A driving mechanism can be provided for selectively translating femoral component 16 relative to tibial component 14. In particular, a top portion of the driving mechanism can be coupled to femoral component 16 via arm 18, while base 12, which is coupled to tibial component 14 can ride independently thereof on the driving mechanism. The illustrative driving mechanism can include a pinion gear 22 (FIG. 1) in base 12 that cooperates with a linear rack 24 on shaft 20. In use, a hex driver or another suitable tool can be used to turn gear 22, and gear 22 meshes with rack 24 to drive rack 24 vertically along arrows V, V'. In certain examples, instrument 10 may be opened to apply a tension load to the patient's knee joint of about 40 lbs., about 60 lbs., about 80 lbs., or more, although the load may vary depending on the surgeon's preference, the state of the patient's surrounding soft tissue, and other factors.

In some instances, a locking mechanism can also be incorporated in the instrument 10 to hold femoral component 16 in place relative to tibial component 14. The illustrative locking mechanism can include a spring-biased lever 40 having an actuator end 42 and a pawl end (not shown). The locking mechanism can allow instrument 10 to be freely opened, but can prevent instrument 10 from being closed until lever 40 is operated by the user. In some instances, the pawl (not shown) can permit vertically upward movement of femoral component 16 along arrow V when opening instrument 10 but resists vertically downward movement of femoral component 16 along arrow V' when closing instrument 10. In some cases, when actuator end 42 of lever 40 is pressed inwardly by the user, the pawl (not shown) of lever 40 can disengage from a ratchet or similar feature, thereby permitting vertically downward movement of femoral component 16 to close instrument 10. Other suitable locking mechanisms can include a detent mechanism or another suitable mechanical mechanism, for example.

In some instances, a distance measuring component can be provided to measure a distance or gap G (FIGS. 7 and 8) between tibial component 14 and femoral component 16 along arrows V, V'. The illustrative distance measuring component can include a distance scale 26 on arm 18 having corresponding values and a pointer 28 on base 12. As shaft 20 of arm 18 translates relative to base 12 along arrows V, V', distance scale 26 can move relative to pointer 28 on base 12. The gap G may be determined by reading the value from distance scale 26 that is aligned with the top end of pointer 28.

In addition to the ability of femoral component 16 to translate vertically relative to tibial component 14, femoral component 16 can also be configured to rotate relative to tibial component 14. More particularly, femoral component 16 can also be configured to rotate relative to arm 18 and tibial component 14 about axis A of FIGS. 1 and 2. As shown in FIG. 2, post 30 can extend into femoral component 16 from arm 18 along the rotation axis A. Femoral component 16 can be configured to rotate around post 30 and rotation axis A. In some instances, the rotation axis A of femoral component 16 can be substantially perpendicular to the translation axis defined along arrows V, V' of femoral component 16.

An angle measuring component, such as a scale plate 32, can be provided to measure an angle α between tibial component 14 and femoral component 16 about the rotation axis A. Scale plate 32 can define an arcuate slot 34, and can include a pointer 36 on femoral component 16. As femoral component 16 rotates relative to arm 18 about axis A, pointer 36 can move along or through the arcuate slot 34 of scale plate 32. The angle α can be determined by reading the value from scale plate 32 that is adjacent to pointer 36. Angle α can indicate a varus/valgus angle of the patient's knee joint and/or internal/external rotation of the patient's knee joint.

Instrument 10 can include a set of modular accessories; examples of some of these accessories are described in further detail below. Instrument 10 and the accessories can be provided together as a system. In this manner, a surgeon or another user can select a first accessory from the system and attach that first accessory to instrument 10. As the surgical procedure progresses, the surgeon can select a second accessory from the system and attach the second accessory to instrument 10 or to the first accessory. Thus, in some examples, the first accessory can be left in place when the second accessory is attached. A variety of different coupling mechanisms (e.g., dovetail joints) and locking mechanisms (e.g., keys, ball detents) can be used to selectively receive and retain the desired modular accessory on instrument 10. Additional information regarding modular accessories for instrument 10 can be found in PCT Publication No. WO2013013094 to Claypool et al., entitled "Knee Arthroplasty Instrument," the disclosure of which is incorporated herein by reference in its entirety.

Figure 3:
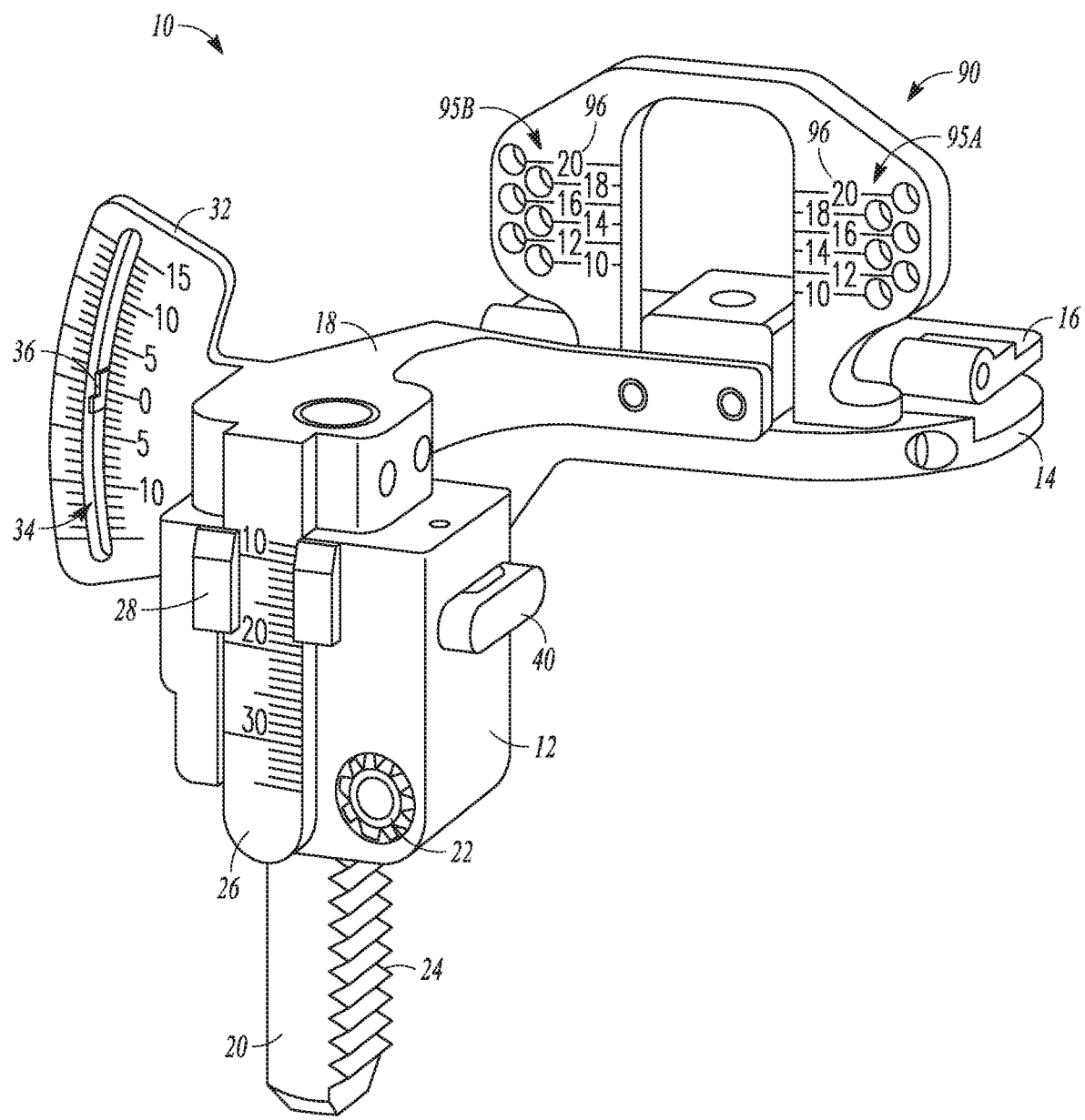
FIG. 3 is a perspective view of a gap sizer, in accordance with an example of the present disclosure mounted to the instrument of FIG. 1.

FIG. 3 is a perspective view of instrument 10 with a gap sizer 90 mounted thereon. Gap sizer 90 can comprise one modular accessory of instrument 10 and can be a pure gap type (PG-type) sizer. The gap sizer 90 can include a plurality of distal-referencing indicators, (e.g., holes 95A and 95B) for referencing the femur. Corresponding holes 95A and 95B can be arranged in horizontal rows 96 as well as vertical columns. In some instances, each row 96 can correspond to a component size, with the row 96 closest to tibial component 14 corresponding to a relatively small component size (e.g., size 10), and the row 96 farthest from tibial component 14 corresponding to a relatively large component size (e.g., size 20). In other instances, each row 96 can correspond to a vertical distance from tibial component 14, with the row 96 closest to tibial component 14 corresponding to a relatively small distance, and the row 96 farthest from tibial component 14 corresponding to a relatively large distance. Thus, rows 96 of holes 95A and 95B can serve as an anterior/posterior (A/P) sizing scale of the gap sizer 90. In some instances, the holes 95A and 95B can comprise reference holes when the sizer is used as a drill guide as will be discussed subsequently.

The gap sizer 90 can be removeably coupled to tibial component 14 of instrument 10, such that the gap sizer 90 remains both vertically and rotatably fixed relative to tibial component 14. Therefore, the gap sizer 90 can be fixedly coupled to tibial component 14. As illustrated in FIG. 3, the gap sizer 90 can be attached to tibial component 14 by sliding legs (not shown) on the gap sizer 90 into corresponding openings 98 in tibial component 14 (FIG. 2). Other coupling mechanisms can also be used between the gap sizer 90 and tibial component 14. Thus, the gap sizer 90 can be selectively retained or locked in place. For example, the gap sizer 90 can be locked onto openings 98 of tibial component 14 by aligning recesses (not shown) in the legs of the gap sizer 90 with corresponding locks 99 on tibial component 14 (FIG. 2). Each lock 99 may be in the form of a ball detent, a spring pin, or another suitable locking mechanism, for example. When removal of the gap sizer 90 is desired, the locks 99 can be released and freed from the legs of the gap sizer 90.

Figure 4:
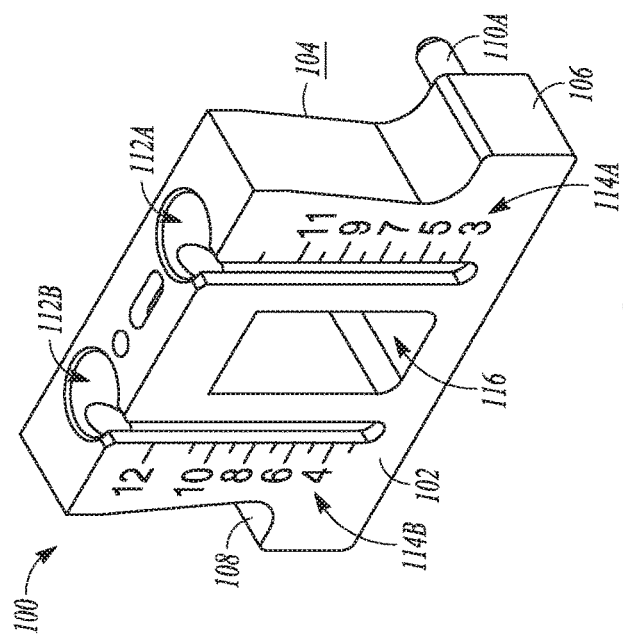
FIG. 4 is a perspective view of a femoral sizer, in accordance with an example of the present disclosure.
Figure 4C:
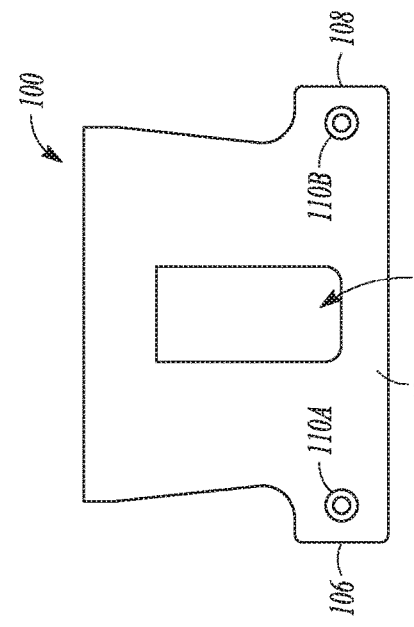
FIG. 4C is a plan view of a third side of the femoral sizer of FIG. 4.

FIGS. 4-4C illustrate a femoral sizer 100, in accordance with an example of the present disclosure. The femoral sizer 100 can comprise another modular accessory of instrument 10. As will be discussed subsequently, the femoral sizer 100 can be coupled to the gap sizer 90. This enables the femoral sizer 100 to determine the size of the femur based on the desired flexion gap G (FIG. 8) without having to take a measurement from the posterior condyles. Thus, the size of the femur can be determined based on the desired flexion gap G independent of the size of the posterior condyles.

Figure 4B:
FIG. 4B is a plan view of a second side of the femoral sizer of FIG. 4.
Figure 4A:
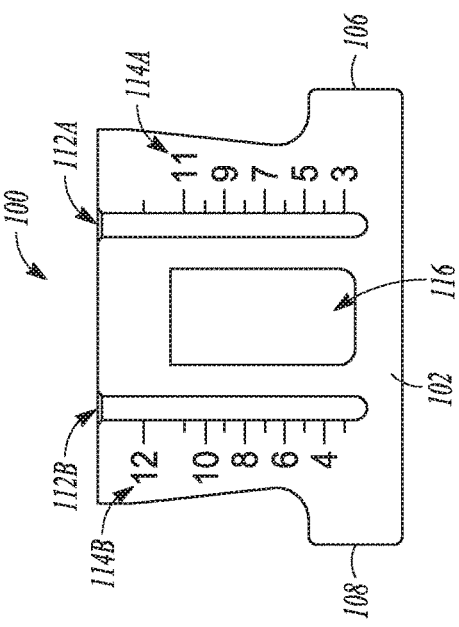
FIG. 4A is a plan view of a first side of the femoral sizer of FIG. 4.

Femoral sizer 100 can include a first face 102, a second face 104, a third face 106, a fourth face 108, pins 110A and 110B, receptacles 112A and 112B, and a scale 114A and 114B. Femoral sizer 100 can have a symmetrical shape as illustrated in FIGS. 4-4C with a shared common central aperture 116 (FIGS. 4, 4A, and 4C). Common central aperture 116 can allow for weight reduction and can enhance visualization. Femoral sizer 100 can be bounded on several sides by first, second, third, and fourth faces 102, 104, 106, and 108. First face 102 can have a similar shape as second face 104. Similarly, third face 106 and fourth face 108 can have similar shapes.

Figure 10:
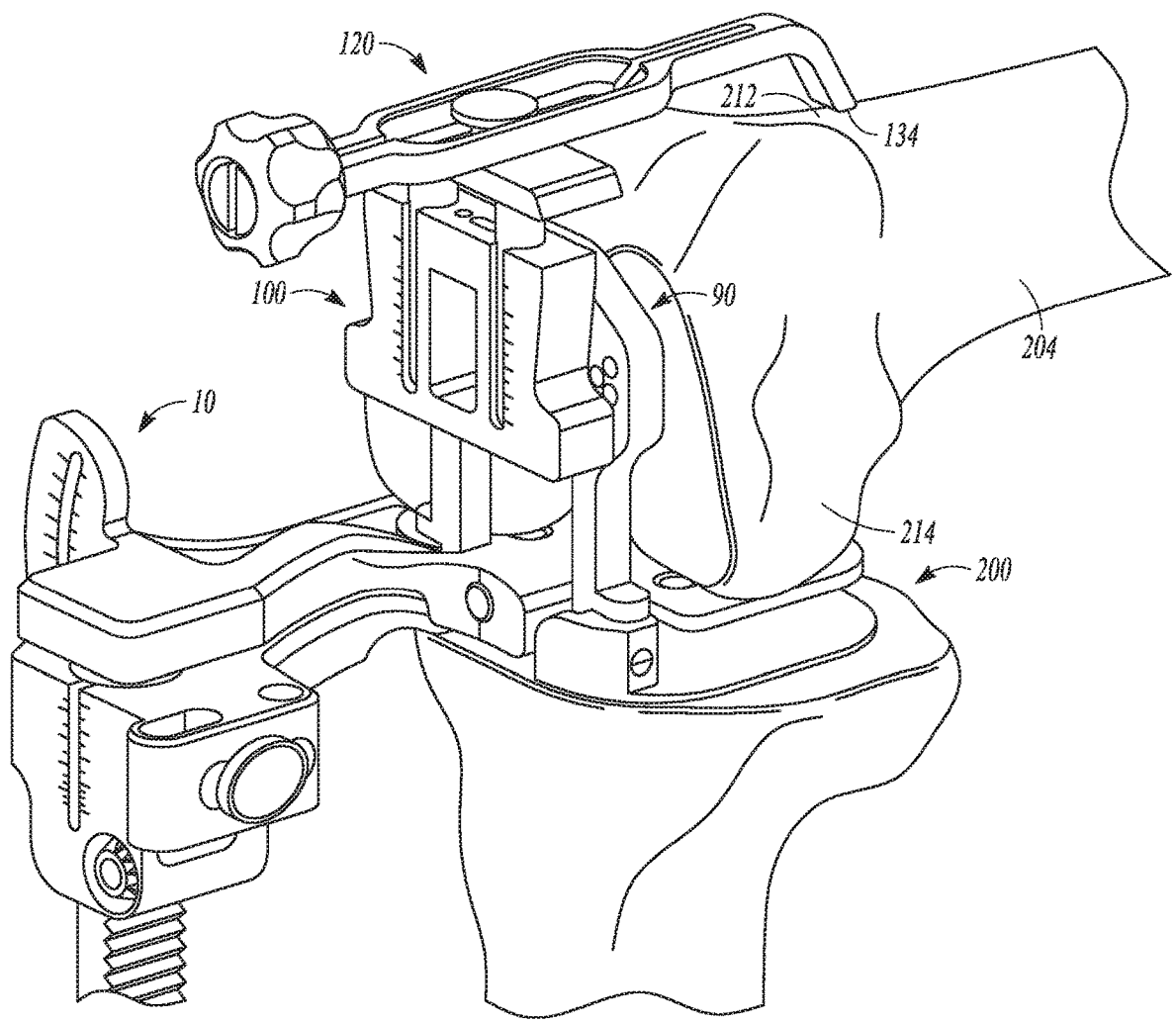
FIG. 10 is a perspective view of the instrument of FIG. 1 with the femoral sizer of FIG. 4 and stylus assembly of FIG. 5 mounted to the gap sizer of FIG. 3 and positioned adjacent the knee joint in flexion, in accordance with an example of the present disclosure.
Figure 10A:
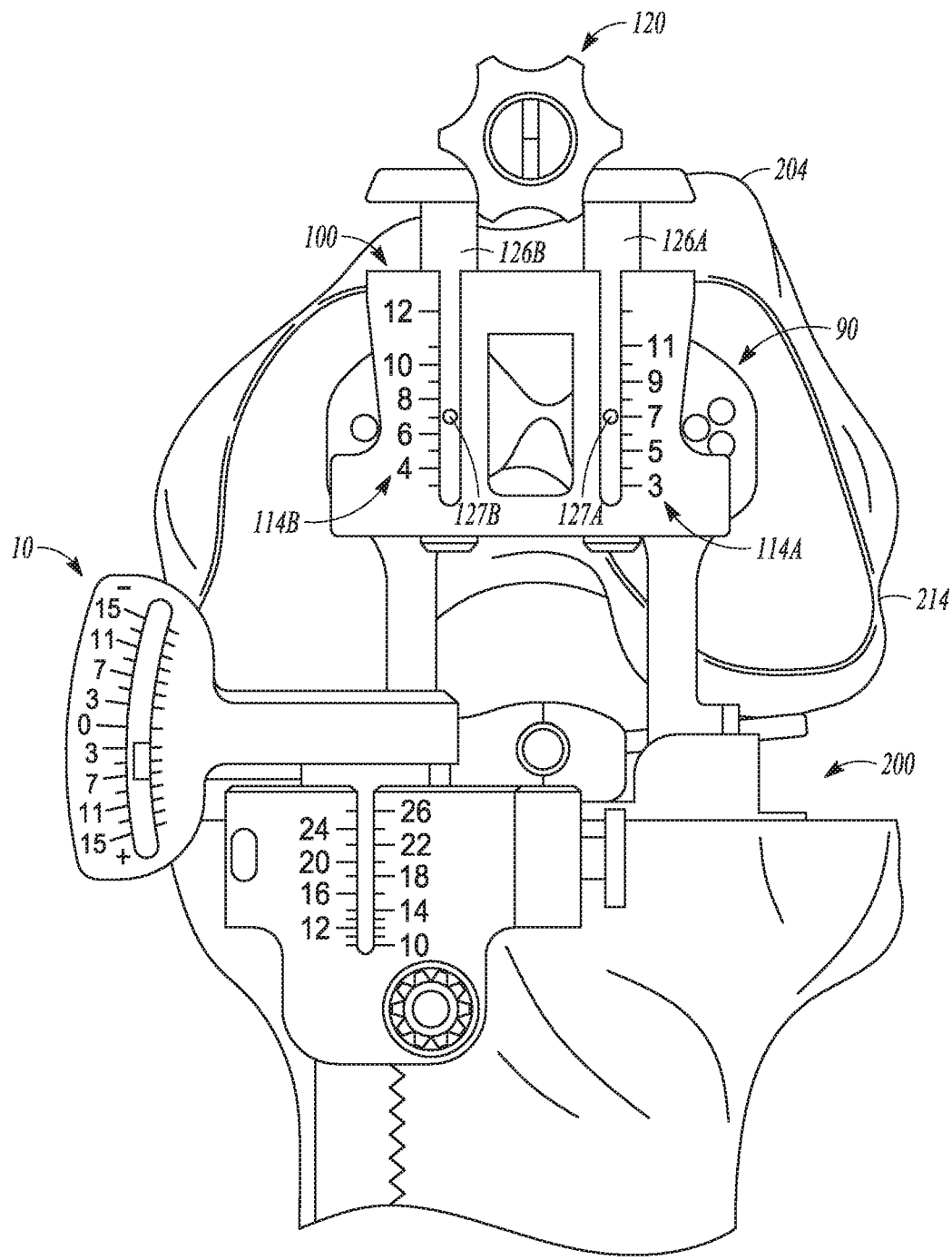
FIG. 10A is a plan distal view of the instrument, femoral sizer, stylus assembly, and gap sizer, in accordance with an example of the present disclosure.

Pins 110A and 110B can extend from second face 104 away from femoral sizer 100. Pins 110A and 110B are similarly shaped and sized and are configured (sized, spaced, toleranced, etc.) to insert into and be received by holes 95A and 95B (FIG. 3) of gap sizer 90 as illustrated in FIGS. 10 and 10A. As illustrated in FIGS. 10 and 10A, pins 110A and 110B are configured to allow femoral sizer 100 to mount on gap sizer 90.

The femoral sizer 100 can define receptacles 112A and 112B that can open to an upper face of the femoral sizer 100 such that the receptacles 112A and 112B are generally vertically oriented (see e.g., FIGS. 4 and 4A). Receptacles 112A and 112B can be disposed to either side of central aperture 116. As illustrated in FIGS. 4 and 4A, the receptacles 112A and 112B can partially open to the first face 102. As will be illustrated subsequently, receptacles 112A and 112B are configured to receive posts of a stylus assembly therein and can allow the posts to be adjusted generally vertically relative to the femoral sizer 100. Scale 114A and 114B can be disposed adjacent receptacles 112A and 112B, respectively. Scale 114A and 114B can be disposed on first face 102 to be visible to the surgeon even when mounted on gap sizer 90 (FIGS. 10 and 10A) and can act as a reference indicator for femoral size.

Figure 5:
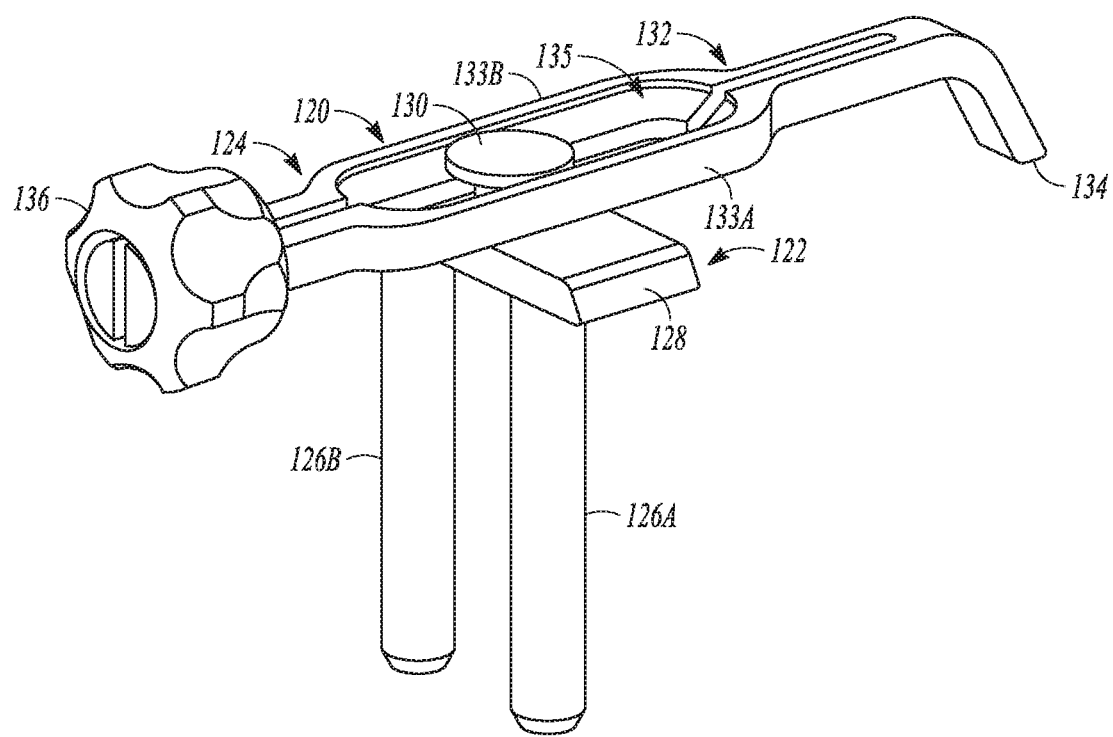
FIG. 5 is a perspective view of a stylus assembly, in accordance with an example of the present disclosure.

FIG. 5 illustrates a stylus assembly 120, in accordance with an example of the present disclosure. Stylus assembly 120 can include a first component 122 and a second component 124. The first component 122 can include posts 126A and 126B, member 128, pin 130. The second component 124 can include a body 132, a stylus head 134, and a knob 136.

First component 122 is adapted to be received in femoral sizer 100 (see FIGS. 10 and 10A) and can be translated substantially vertically (as indicated by arrows V, V' of FIG. 1) relative thereto. Second component 124 can be configured to connect to first component 122 and can be translated substantially horizontally relative to the first component 122 and femoral sizer 110. In some instances, second component 124 can be configured to rotate relative to first component 122, femoral sizer 110, and other components of instrument 10.

As illustrated in the example of FIG. 5, posts 126A and 126B can extend generally vertically and are connected to member 128. Posts 126A and 126B can be configured to be received in receptacles 112A and 112B (FIGS. 4, 4A), respectively. As will be discussed subsequently, posts 126A and 126B can be provided with indicative marks that, together with scale 114A and 114B (FIGS. 4 and 4A) can be used as reference indicators for the femur to determine the size of the femur. Member 128 can extend in a generally transverse direction between posts 126A and 126B. In some examples, member 128 can be integrally formed with posts 126A and 126B.

Pin 130 can extend generally vertically from member 128 and can be connected thereto. In some instances pin 130 can be integrally formed from member 128. In some cases, such as illustrated in FIG. 5, pin 130 can include a reduced diameter body portion (not shown) and an increased diameter head portion. Pin 130 can be received in and selectively affixed to second component 124.

Second component 124 can include a symmetrical design and can extend generally horizontally from stylus head 134 to knob 136. Pin 130 can be configured to be received between tangs 133A and 133B of body 132. In particular, body 132 can include first and second portions (e.g., tangs 133A and 133B) adapted to form a guide track 135 therebetween. Pin 130 can be configured to reside in guide track 135. Knob 136 can be configured to selectively force tangs 133A and 133B against pin 130. In some instances, knob 136 can also be adjusted to reduce force exerted by tangs 133A and 133B to allow body 132 to be translated relative to pin 130 to allow for horizontal and/or rotational adjustment of second component 124 (e.g., movement of stylus head 134 to a desired position adjacent the femur) relative to first component 122 (and other components of instrument 10).

Figure 6:
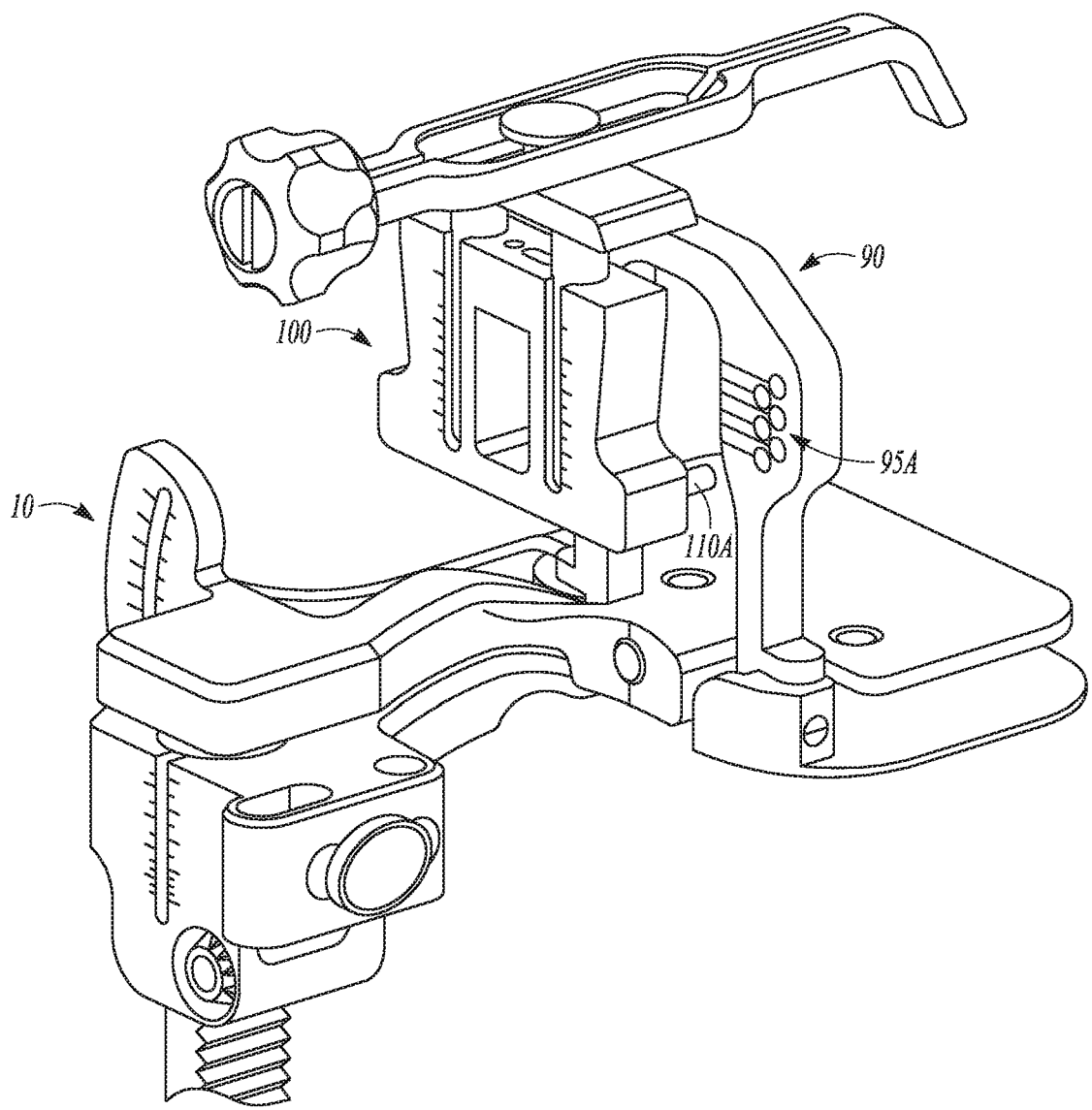
FIG. 6 is a perspective view of the stylus assembly of FIG. 5, the femoral sizer of FIG. 4, and the gap sizer of FIG. 3 assembled to the instrument of FIG. 1.
Figure 8:
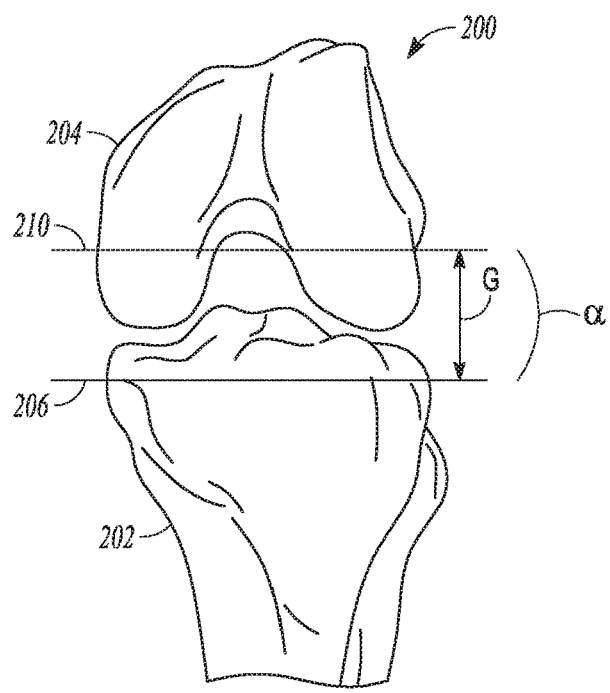
FIG. 8 is an anterior elevated view of the knee joint in flexion, in accordance with an example of the present disclosure.

FIG. 6 shows a portion of instrument 10 having femoral sizer 100 and gap sizer 90 positioned adjacent thereto. As discussed, femoral sizer 100 and gap sizer 90 can comprise first and second accessories for instrument 10. As illustrated, gap sizer 90 can be affixed to instrument 10. Femoral sizer 100 can be aligned so as to have pins 110A and 110B (FIGS. 4, 4B, and 4C) installed in distal referencing holes 95A and 95B (95B not shown in FIG. 6) that comprise the appropriate holes selected based upon the selected flexion gap G (FIG. 8). As the referencing holes 95A and 95B are referenced from the tibial component 14 rather than from the posterior condyles, the arrangement of the femoral sizer 100 mounted on the gap sizer 90 (at referencing holes 95A and 95B) can enable the femoral sizer 100 to determine the size of the femur without measurement from the posterior condyles.

Figure 7:
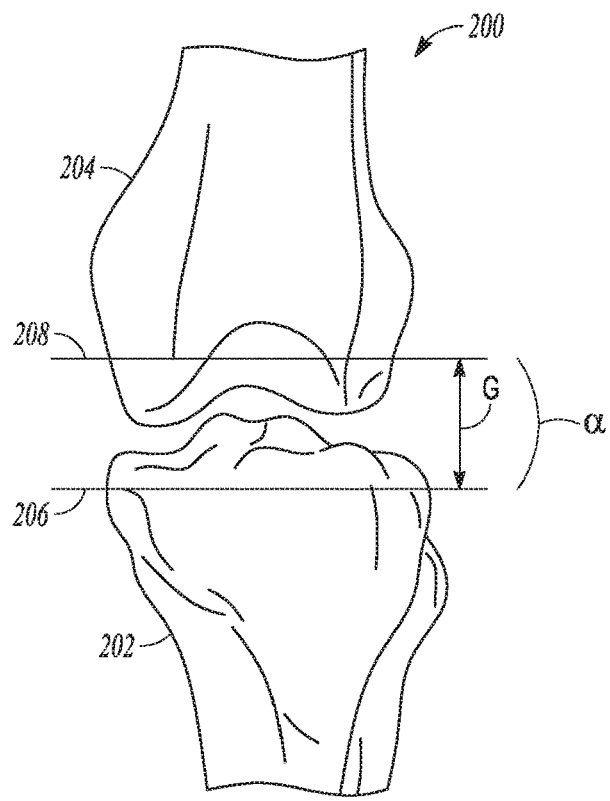
FIG. 7 is an anterior elevated view of a knee joint in extension, in accordance with an example of the present disclosure.

FIG. 7 illustrates a knee joint 200 in extension as viewed from the anterior thereof. Similarly, FIG. 8 illustrates knee joint 200 in flexion as viewed from the anterior thereof. To obtain the views of FIGS. 7 and 8, a surgeon can expose tibia 202 and femur 204 of the knee joint 200. This can involve pre-operative planning, incising the patient's skin, incising the patient's joint capsule, and removing osteophytes, for example.

With the knee joint 200 exposed, the surgeon can use instrument 10 to separate tibia 202 and femur 204 of the patient's knee joint 200 to a predetermined tension, and to plan and identify the desired bone resections of tibia 202 and femur 204. With the patient's knee joint 200 tensioned in extension (FIG. 7), the surgeon can plan and identify a proximal tibial resection 206 and a distal femoral resection 208 that will produce a desired gap G and angle α therebetween. As discussed previously, the extension angle α can be referred to as a varus/valgus angle in some instances. With the patient's knee joint 200 tensioned in flexion (FIG. 8), the user is able to plan and identify the proximal tibial resection 206 and a posterior femoral resection 210 that will produce a desired gap G and angle α therebetween. The flexion angle α can be referred to as an internal/external rotation angle. Gap G and angle α between tibia 202 and femur 204 can be selected based on the patient's age, the patient's bone quality, the state of the patient's surrounding soft tissue, the types of prosthetic implants being used, and other factors, for example.

Tibia 202 and femur 204 can be resected using suitable cut guides. For example, the Minimally Invasive Surgery (MIS) Tibial Cut Guide Assembly, which is available from Zimmer, Inc. of Warsaw, Ind., can be used to form the proximal tibial resection 206 in tibia 202. Suitable cut guides can also be used to form the distal femoral resection 208 and the posterior femoral resection 210 in femur 204. In addition to evaluating bone resections, the surgeon can also evaluate soft tissue resections, releases, or other soft tissue operations that can impact gap G and angle α between tibia 202 and femur 204. For example, if the surgeon desires a larger gap G between tibia 202 and femur 204 without resecting more bone from tibia 202 or femur 204, the surgeon may release or otherwise relax ligaments around the patient's knee joint 200.

According to examples of the present disclosure, knee joint 200 can be prepared such that gap G and angle α between tibia 202 and femur 204 are the same or substantially the same in extension (FIG. 7) as in flexion (FIG. 8). For example, a three-dimensional space can be maintained between tibia 202 and femur 204 in extension and flexion, the size of this space can vary depending upon the anatomy of the patient. Thus, a surgeon implanting a prosthetic femoral implant having equally thick distal and femoral condyles can prepare an extension gap G that is the same as the flexion gap G, while a surgeon implanting a prosthetic femoral implant having distal and femoral condyles of different thicknesses can prepare an extension gap G that is not the exactly the same as the flexion gap G to account for the different thicknesses. When angle α is 0 degrees, such that the proximal tibial resection 206 is parallel to the distal femoral resection 208 in extension (FIG. 7) and the posterior femoral resection 210 in flexion (FIG. 8), the three-dimensional space between tibia 202 and femur 204 can be rectangular in shape in extension and flexion. It is also contemplated that the surgeon can tolerate differences between the extension angle α (FIG. 7) and the flexion angle α (FIG. 8), such as differences of a few degrees.

It should be noted that instrument 10 and its accessories can be used before and/or after resecting or otherwise manipulating knee joint 200. For example, before resecting or otherwise manipulating knee joint 200, instrument 10 can be used to measure the natural gap G and angle α between tibia 202 and femur 204 in tension. Also, instrument 10 can be used to plan or identify the proximal tibial resection 206, the distal femoral resection 208, the posterior femoral resection 210, and/or any soft tissue resections that will produce a desired gap G and angle α between tibia 202 and femur 204 in tension. After resecting or otherwise manipulating knee joint 200, instrument 10 can be used to verify the desired gap G and angle α between tibia 202 and femur 204 in both extension and/or flexion.

Additionally, as will be discussed subsequently, the instrument 10 with accessories including gap sizer 90 (FIG. 3) and femoral sizer 100 (FIGS. 4-4C) can aid the surgeon in sizing the patient's femur 204, in determining a location and orientation of certain femoral resections, in selecting an appropriately sized femoral cut guide, in determining the location and orientation of the femoral cut guide relative to the patient's femur 204, and in selecting the location and orientation of an appropriately sized prosthetic femoral implant corresponding to the femoral cut guide, for example.

Figure 9:
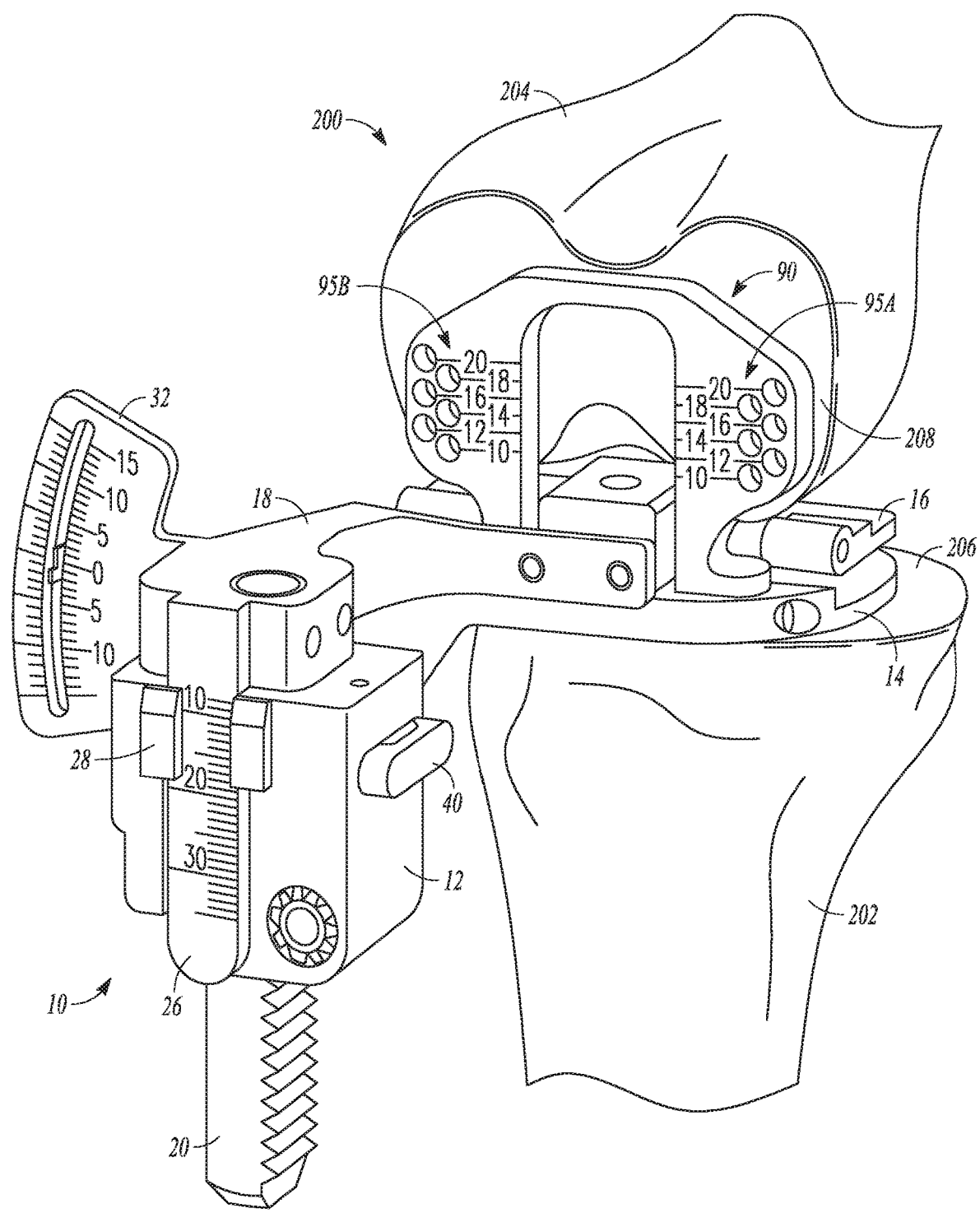
FIG. 9 is a perspective view of the instrument of FIG. 1 with the gap sizer according to FIG. 3 positioned adjacent the knee joint in flexion, in accordance with an example of the present disclosure.

FIG. 9 illustrates gap sizer 90 positioned adjacent the knee joint 200 in flexion. Gap sizer 90 can be attached to instrument 10 as illustrated in FIG. 9 (see also FIG. 3). With the patient's knee joint 200 in flexion, tibial component 14 of instrument 10 can be positioned against the patient's tibia 202, and femoral component 16 of instrument 10 can be placed against the patient's uncut posterior femur 204. Although FIG. 9 shows femoral component 16 of instrument 10 in contact with the patient's posterior femur 204, a femoral plate or other accessory can be attached to femoral component 16 of instrument 10 to directly contact the patient's posterior femur 204 in some examples. Although shown in flexion, the patient's knee joint 200 can also be moved to extension with gap sizer 90.

Based on the size of the patient's femur 204 (see e.g., discussion with regard to FIGS. 10 and 10A) and the gap G produced when the patient's knee joint 200 is tensioned in flexion and/or extension (see e.g., discussion with regard to FIGS. 7 and 8), the surgeon may identify an appropriate row 96 of distal-referencing holes 95A and 95B in gap sizer 90 and select the corresponding cut guide. For example, after forming the distal femoral resection 208 in femur 204, the surgeon can measure the extension gap G produced when the patient's knee joint 200 is tensioned in extension. Then, the surgeon can tension the patient's knee joint 200 in flexion to the same tension as in extension and select the row 96 of distal-referencing holes 95A and 95B in gap sizer 90 that correspond to the previously-measured extension gap G. The surgeon can also use the selected distal-referencing holes 95A and 95B in gap sizer 90 as guides to mark or drill distal fixation holes (not shown) into the patient's femur 204 for eventual receipt of a cut guide (not shown), thereby arriving at a posterior femoral resection 210 (FIG. 8) that produces substantially a same flexion gap G as the previously measured extension gap G. Because gap sizer 90 can be coupled to tibial component 14 of instrument 10, rotation or translation of the patient's femur 204 on femoral component 16 will not rotate or translate gap sizer 90.

FIGS. 10 and 10A illustrate femoral sizer 100 and stylus assembly 120 mounted to gap sizer 90 and positioned adjacent the knee joint in flexion. In particular, FIG. 10 provides an elevated perspective view and FIG. 10A provides a plan view from a distal location.

FIGS. 10 and 10A illustrate gap sizer 90 can be mounted to instrument 10 (only a portion of instrument 10 is shown in FIGS. 10 and 10A) in the arrangement previously described in reference to FIGS. 3 and 9. Femoral sizer 100 can be mounted to gap sizer 90 with pins 110A and 110B (FIGS. 4, 4B, and 4C) installed in distal referencing holes 95A and 95B (95B not shown in FIG. 10) that comprise the appropriate holes selected based upon the selected flexion gap G (FIG. 8). Stylus assembly 120 can be moveably mounted in femoral sizer 100. Although not illustrated, in some cases stylus assembly 120 can include fixture features (clamps, bars, tabs, detents, etc.) that can allow the surgeon to selectively affix stylus assembly 120 to femoral sizer 100 as desired.

As illustrated in FIG. 10, stylus assembly 120 can be adjusted relative to femoral sizer 100, gap sizer 90, instrument 10 etc., such that stylus head 134 is placed against or adjacent the patient's anterior femoral cortex 212. Then, as shown in FIG. 10A, the surgeon can utilize reference indicators such as scale 114A and 114B on femoral sizer 100 and markings 127A and 127B on posts 126A and 126B of stylus assembly 120 to size the patient's femur 204 for selection of an appropriately sized cut guide. Although not shown in the examples provided, the arrangement of scale and markings can be reversed such that the posts are provided with a scale and the femoral sizer is provided with markings. In some cases, the femoral sizer 100 can be coupled directly to the instrument 10 rather than the gap sizer 90. In such an arrangement, the femoral sizer 100 could still be referenced from the gap sizer 90 such as at one or more reference indictors (e.g., referencing holes 95A and/or 95B).

As discussed previously, as the referencing holes 95A and/or 95B (to which femoral sizer 100 is mounted) are referenced from the tibial component 14 rather than from the posterior condyles, the arrangement of the femoral sizer 100 referenced from the gap sizer 90 (at referencing holes 95A and/or 95B) can enable the femoral sizer 100 to determine the size of the femur 204 without measurement from the posterior condyles 214 (only one condyle shown in FIGS. 10 and 10A). This enables the femoral sizer 100 to determine the size of the femur 204 based on the desired flexion gap G (FIG. 8), independent of the posterior condyles, which no longer serve as the reference surfaces. Thus, the complexity of TKA procedures using the gap balancing technique can be reduced.

Description of additional accessories including examples of cut guides and their use with the instrument 10 can be found in PCT Publication No. WO2013013094 to Claypool et al., entitled "Knee Arthroplasty Instrument," the disclosure of which is incorporated herein by reference in its entirety.

The above Detailed Description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more."

In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A knee arthroplasty system for use in a patient's knee joint, the knee joint including a tibia and a femur, the system comprising:
   a tool including a tibial component configured for placement against the tibia and a femoral component configured for placement against the femur, the femoral component being moveably coupled to the tibial component to place the patient's knee joint in tension by separating the tibia and the femur;
   a first accessory mountable to the tool, wherein the first accessory comprises a gap sizer with a plurality of holes for referencing the femur, wherein the plurality of holes are arranged in horizontal rows as well as vertical columns on either side of an opening of the gap sizer; and
   a second accessory configured to couple with the first accessory with a plurality of pins each of which is insertable in one of the plurality of holes, wherein when the first accessory is mounted to the tool and when the second accessory is coupled to the first accessory, together the second accessory and the first accessory work in tandem to reference the femur for determining a size of the femur.

2. The system of claim 1, wherein a portion of the second accessory is configured to be slideably coupled to the first accessory for constrained anterior-posterior movement relative thereto.

3. The system of claim 1, wherein determining the size of the femur does not include having to determine a size of a posterior condyle of the femur.

4. The system of claim 1, wherein the first accessory is rotatably and translationally fixed relative to the tibial component such that the femoral component is capable of one or more of rotation and translation relative to the first accessory.

5. The system of claim 1, wherein the second accessory includes a stylus that is rotatable and translatable relative to the first accessory.

6. The system of claim 5, wherein the stylus comprises:
   a first component having at least one post configured to be received in a receptacle of the first accessory and moveable within the receptacle relative to the first accessory; and
   a second component adapted for anterior referencing and being moveably coupled to the first component and configured to contact an anterior surface of the femur at or adjacent an anterior cortex of the femur.

7. The system of claim 6, wherein the second component comprises:
   a body having first and second tangs that define a guide track adapted to receive a portion of the first component; and
   a knob configured to selectively exert force on the first and second tangs to force the first and second tangs against the first component.

8. The system of claim 1, wherein the second accessory comprises:
   a body having at least one receptacle adapted to receive a moveable portion of the second accessory therein; and
   wherein a reference indicator is formed by the moveable portion of the second accessory and the body and comprises a sizing scale disposed along a face of the body and a reference mark on the portion of the moveable portion of the second accessory.

9. A knee arthroplasty system for use in a patient's knee joint, the knee joint including a tibia and a femur, the system comprising:
- a tool including a tibial component configured for placement against the tibia and a femoral component configured for placement against the femur, the femoral component being moveably coupled to the tibial component to place the patient's knee joint in tension by separating the tibia and the femur;
- a first accessory useable with the tool; and
- a second accessory configured to couple with and be moveable relative to the first accessory;
- wherein the first accessory has a first reference indicator and the second accessory has a second reference indicator, and wherein together the first reference indicator and second reference indicator indicate a size of the femur when the second accessory is placed at or adjacent an anterior cortex of the femur and the second accessory is coupled with the first accessory;
- wherein the second accessory comprises a stylus, the stylus comprising:
  - a first component having at least one post configured to be received in a receptacle of the first accessory and moveable within the receptacle relative to the first accessory; and
  - a second component adapted for anterior referencing and being moveably coupled to the first component and configured to contact an anterior surface of the femur at or adjacent the anterior cortex of the femur, wherein the second component comprises:
    - a body having first and second tangs that define a guide track adapted to receive a portion of the first component; and
    - a knob configured to selectively exert force on the first and second tangs to firmly abut the first and second tangs against the first component.

10. The system of claim 9, wherein the first accessory comprises:
- a body having at least one receptacle adapted to receive a portion of the second accessory therein; and
- wherein a reference indicator is formed by the first accessory and the second accessory and comprises a sizing scale disposed along a face of the first accessory and a reference mark on the portion of the second accessory.

11. The system of claim 9, wherein a portion of the second accessory is configured to be slideably moveable relative to the first accessory for constrained anterior-posterior movement relative thereto.

12. The system of claim 9, wherein determining the size of the femur does not include having to determine a size of a posterior condyle of the femur.

13. The system of claim 9, wherein the first accessory is rotatably and translationally fixed relative to the tibial component such that the femoral component is capable of one or more of rotation and translation relative to the first accessory.

14. A knee arthroplasty system for use in a patient's knee joint, the knee joint including a tibia and a femur, the system comprising:
- a tool including a tibial component configured for placement against the tibia and a femoral component configured for placement against the femur, the femoral component being moveably coupled to the tibial component to place the patient's knee joint in tension by separating the tibia and the femur;
- a first accessory mountable to the tool, wherein the first accessory comprises a clap sizer with a plurality of holes for referencing the femur, wherein the plurality of holes are arranged in horizontal rows as well as vertical columns on either side of an opening of the gap sizer; and
- a second accessory having a first portion configured to couple with the first accessory, a second portion that is moveable relative to the first portion and the first accessory in a first direction and a third portion that comprises a stylus that is rotatable and translatable in at least a second direction relative to the first accessory, the first portion and the third portion, wherein when the first accessory is mounted to the tool and when the second accessory is coupled to the first accessory together the second accessory and the first accessory work in tandem to reference the femur for determining a size of the femur.

15. The system of claim 14, wherein the first accessory is rotatably and translationally fixed relative to the tibial component such that the femoral component is capable of one or more of rotation and translation relative to the first accessory.

16. The system of claim 14, wherein the first accessory has a first reference indicator and the second accessory has a second reference indicator, and wherein together the first reference indicator and second reference indicator indicate a size of the femur when the second accessory is placed at or adjacent an anterior cortex of the femur and the second accessory is coupled with the first accessory.

* * * * *

UNITED STATES PATENT AND TRADEMARK OFFICE
CERTIFICATE OF CORRECTION

PATENT NO. : 10,952,755 B2
APPLICATION NO. : 16/108861
DATED : March 23, 2021
INVENTOR(S) : Jason S. Toler Page 1 of 1

It is certified that error appears in the above-identified patent and that said Letters Patent is hereby corrected as shown below:

In the Claims

In Column 16, Line 19, in Claim 14, delete "clap" and insert --gap-- therefor

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*